United States Patent [19]

Bretzloff, deceased

[11] Patent Number: 4,617,047

[45] Date of Patent: Oct. 14, 1986

[54] MUSHROOM SUPPLEMENT

[75] Inventor: Carl W. Bretzloff, deceased, late of Napoleon, Ohio, by Lillian Bretzloff, executrix

[73] Assignee: Campbell Soup Company, Camden, N.J.

[21] Appl. No.: 711,006

[22] Filed: Mar. 12, 1985

Related U.S. Application Data

[63] Continuation-in-part of Ser. No. 402,314, Jul. 27, 1982, Pat. No. 4,534,781.

[51] Int. Cl.⁴ ............................................. C05G 3/00
[52] U.S. Cl. ........................................................ 71/5
[58] Field of Search ................... 71/5, 64.02, 64.07; 47/1.1, 57.6; 426/309, 132, 63, 69

[56] References Cited

U.S. PATENT DOCUMENTS

| | | | |
|---|---|---|---|
| 2,648,163 | 8/1953 | Szuecs | 47/1.1 |
| 3,560,190 | 2/1971 | Hughes et al. | 71/5 |
| 3,942,969 | 3/1976 | Carroll, Jr. et al. | 71/5 |
| 4,000,319 | 12/1976 | Eichelburg | 426/2 |
| 4,059,919 | 11/1977 | Green | 47/1.1 |
| 4,139,641 | 2/1979 | Zeeh et al. | 426/69 |
| 4,154,863 | 5/1979 | Kahn et al. | 426/327 |
| 4,333,757 | 6/1982 | Kurtzman, Jr. | 71/5 |
| 4,337,594 | 7/1982 | Hanacek et al. | 47/1.1 |
| 4,420,319 | 12/1983 | Holtz | 71/5 |
| 4,534,781 | 8/1985 | Wu et al. | 71/5 |

FOREIGN PATENT DOCUMENTS

WO82/00637 3/1982 PCT Int'l Appl. ...................... 71/5

OTHER PUBLICATIONS

Carroll, Jr., "Improving Post-Composting Mushroom Supplements for Use at Spawning", M.A. Thesis, Pennsylvania State University, 1973.

*Primary Examiner*—Ferris H. Lander
*Attorney, Agent, or Firm*—Banner, Birch, McKie & Beckett

[57] ABSTRACT

An improved nutrient supplement is disclosed for enhancing the growth of mushroom mycelia in a compost bed comprising a combination of a protein-containing nutrient and a composition for inhibiting the growth of molds in said compost bed. Methods for making said supplement and a process for its use are also disclosed.

8 Claims, No Drawings

MUSHROOM SUPPLEMENT

CROSS-REFERENCES TO RELATED APPLICATIONS

This application is a continuation-in-part of earlier copending application Ser. No. 402,314 filed on July 27, 1982, in the names of Carl W. Bretzloff and Lung-chi Wu, now U.S. Pat. No. 4,534,781 issued on Aug. 13, 1985.

TECHNICAL FIELD

This invention relates to the art of mushroom cultivation and specifically pertains to an improved nutrient source for promoting mushroom growth.

BACKGROUND OF THE INVENTION

The basic procedure for commercially producing mushrooms involves an initial step of impregnating a suitably prepared compost with mushroom mycelia. This step is referred to as "spawning", and is generally done in a plurality of individual beds or trays to facilitate handling and to economize space. The compost provides the nutrients, e.g., amino acids, essential for mycelium growth. The compost is often prepared from a mixture of horse manure and straw suitably treated, according to well known procedures, to yield a final composition promotive of mushroom growth. The mycelium-impregnated compost is then allowed to develop under carefully controlled conditions of temperature and moisture, until the hyphae of the mycelium have permeated the compost. This process usually takes anywhere from two to three weeks. At this time, the mycelia-permeated compost is covered with a thin layer of soil or sand; peat is often used. This step is referred to as "casing", and the presence of this top layer causes the mushrooms to "flower", i.e., to form the fleshy fruiting body harvested as the product. It generally takes about three weeks after the beds are cased for the first mushrooms to appear. After harvesting the first crop of mushrooms, the bed goes through another growth cycle in which additional mushroom fruits are produced. These growth cycles are referred to as "breaks", and a commercial compost bed generally undergoes three to five breaks before the compost becomes significantly depleted in essential nutrients. The compost is then discarded and the procedure is initiated anew.

The prior art has shown that enhanced mushroom yields can be obtained by adding supplementary nutrients to the compost bed. For example, in Hughes et al. U.S. Pat. No. 3,560,190 a dry formulation based on a combination of cottonseed meal and cottonseed oil is disclosed as a suitable supplement. It is also known that cracked soybeans can be used as a supplement, i.e., soybeans that have been broken into smaller pieces of about 1/6 to 1/10 the size of the whole bean. These materials have been added to the compost bed both at the time of spawning and casing.

Nutrient supplementation, however, is susceptible to some undesirable side effects. One problem that has been encountered is excessive bed heating, apparently caused by the ready availability of the nutrient source to the highly active microbial mushroom culture. Temperature excursions above 35° C. (95° F.), sufficient to significantly deplete, if not completely destroy the mushroom mycelia have been observed. Another problem is encountered when adding the supplement to the compost at the time of spawning. In many cases other microorganisms, primarily molds, pre-existing in the compost, introduced with the supplement, or introduced via airborne contamination, compete with the mushroom mycelium for the added nutrients. This reduces the availability of the supplement for its intended purpose and often hinders the development of the mushroom mycelium.

Recognizing these problems, Carroll et al. U.S. Pat. No. 3,942,969 provides a supplement suitable for addition to the compost at the time of spawning, in which the release of the nutrient is delayed. This supplement comprises a denatured protein source, including proteins derived from cottonseed, soybean and peanuts. As disclosed, the denaturing can be accomplished by heating or by treatment with alkalies, acids or formaldehyde. Unfortunately, the potential gains in mushroom yields, are disadvantageously offset by the economic penalty associated with the denaturation treatment.

It is an object of the present invention to provide a mushroom supplement for increasing the yield of mushrooms in commercial mushroom production.

It is a further object of this invention to provide a mushroom supplement that can be added to the compost either at spawning or up to casing.

It is yet another object of this invention to provide a mushroom supplement that is more economical to produce than the denatured protein of Carroll et al.

SUMMARY OF THE INVENTION

These and other objects are met by the present invention which comprises an improved particulate supplement for enhancing the growth of mushroom mycelia in a compost bed comprising the combination of a protein-containing nutrient and a mold inhibitory composition.

In another aspect of the present invention the supplement also may include additional hydrophobic material that may or may not be assimilable by competing microorganisms in the compost, and which may delay the availability of the protein-containing nutrient to the mushroom mycelia while said hydrophobic material is gradually removed from the nutrient under the conditions of mushroom growth.

The present invention also pertains to a method of making the improved supplement and a method for using the supplement to enhance the growth of mushroom mycelia.

Unless otherwise indicated, all percentages are reported by weight.

DETAILED DESCRIPTION

As disclosed, the present invention comprises a nutrient supplement for enhancing the growth of mushroom mycelia. By treating previously known particulate nutrient supplements with a mold inhibitory composition, e.g., by coating cracked soybeans or pelletized soybean fines with such composition, I have found that the supplement can be applied at spawning and the problem of competing microbial attack is successfully avoided. Thus commercial mushroom yields and compost quality can be significantly enhanced. In addition to using the mold inhibitory composition as a coating, the composition may be incorporated throughout a particulate nutrient supplement formed, for example, by pelletizing finely-divided protein-containing particles. The mold inhibitory composition also may be admixed with additional hydrophobic material, which may either be assimilable, e.g., corn or peanut oil, or not assimilable, e.g., a paraffin wax, by organisms in the compost. As used herein, "particulate" means particle sizes on the order of at least about 1/25 and preferably about 1/16 of an inch.

In the broadest aspect of this invention, the protein-containing nutrient supplement comprises any material which is known to beneficially enhance the growth of mushroom mycelia, i.e., materials which satisfy the function of a nutrient. The nutrient supplement also may include materials such as vitamins, minerals, carbohydrates, sugars, etc. Protein-containing nutrients from both vegetable and animal sources are particularly useful. Specific sources of protein-containing nutrients include fish meals, malt sprouts, linseeds, sesame seeds, safflower and sunflower seeds, rape seed and many others. Vegetable protein sources such as cottonseed, soybean and peanuts are particularly advantageous. Although the use of soybeans as the particulate nutrient supplement is specifically referred to throughout the specification, such other materials as described above can also be usefully employed.

As noted, the present invention is specifically directed to the use of compounds, referred to throughout the specification and claims as the "mold inhibitory composition" which, in combination with a protein-containing nutrient used as a mushroom supplement, inhibit the growth of molds without inhibiting the growth of the mushroom fungi. Such molds are commonly encountered in commercial mushroom beds. Applicant has discovered the unexpected result that a wide variety of mold inhibitory agents, including materials such as benzoic acid, undecylenic acid, rosin, stearic acid, methylparaben (methyl parahydroxybenzoate), BENZOFLEX (trademark for dibenzonate esters of dipropylene glycol), boric acid, oxalic acid, salicylic acid, palagonic acid, sulfenamide, calcium oxide, calcium sulfate and the like and mixtures thereof can be used in combination with a protein-containing nutrient as the mold inhibitory composition of this invention to inhibit molds without compromising the growth of the mushroom fungi and yield of mushrooms relative to supplement added. Other suitable compounds useful as the mold inhibitory composition of this invention can be identified by routine experimentation. The net effect is that under commonly encountered conditions in commercial mushroom farms, the mushroom mycelia receive more of the protein-containing nutrient and there is a net increase in mushroom production and compost quality.

The mold inhibitory compounds can be applied, either singly or in combination, to the protein-containing nutrient supplement, which may be pasteurized. Generally, the mold inhibitory composition is applied at a level between about 1 and about 16% by weight of the supplement. Application of too low a level fails to provide the desired effect while the use of higher levels is not economically justified in terms of increased mushroom yield. The optimum level for a particular composition can be identified using routine experimentation. I have found that a combination of benzoic acid and undecylenic acid each applied at a coating level of between about 1% and 8% is particularly effective in suppressing mold and bacterial growth to a suitable degree. Generally, a combination of benzoic acid and undecylenic acid each applied at a coating level of between about 1% and 4% is sufficient.

The mold inhibiting composition can be used in combination with the protein-containing nutrient to obtain a particulate supplement in a variety of ways. For example, it can be applied as a coating on particulate supplements, such as cracked soybeans or pelletized soybean fines. Alternatively, it can be blended with finely divided protein particles, such as soybean fines, before the particles are pelletized to form the particulate supplement. These latter techniques, i.e., the use of pelletized fines as the particulate supplement, permit one to reclaim the nutrient value of the fines recovered from a protein source, e.g., cracked soybeans. Such pelletized supplements will also include a binder material, such as lignin, in the composition. Generally, the direct use of such fines as a nutrient supplement leads to excessive bed heating due to the ready availability of the protein material to competing organisms in the mushroom compost. Other techniques for applying such materials in combination with the protein-containing nutrient as a particulate supplement will be apparent to those skilled in the art.

For example, benzoic acid combined with a hydrophobic material such as an oil can be applied to the nutrient supplement by heating such combination to about 160°–165° F. to dissolve the benzoic acid followed by blending the hot liquid with the supplement material. Preferably, the conditions are adjusted as needed to avoid denaturing the protein-containing nutrient. Usually this means blending the benzoic acid composition with particulate supplements at a temperature between about 75° F. and 115° F. Undecylenic acid is a liquid at ambient conditions and can be mixed directly, with or without other hydrophobic materials, with the supplement material. The mold inhibitory composition also may be applied as a solution using suitable solvents or as a dispersion. The present invention is not limited to any particular technique and other procedures will be apparent to those skilled in the art.

Preferably a mixture of benzoic acid and undecylenic acid is used to coat a particulate supplement. Generally, the mixture includes between about 1% and 8% (by weight) benzoic acid and between about 1% and 8% undecyclenic acid, based on the total weight of the supplement. Other hydrophobic materials also could be added. One suitable procedure for applying this mixture to the protein source to prepare a particulate supplement involves heating the mixture to about 160°–165° F. to dissolve the solid benzoic acid in the oily undecylenic acid. The mixture is then blended with cracked soybeans at a temperature of about 105°–115° F. or is blended with pelletized soybean fines at a temperature of about 65° to about 75° F. While coating, constant stirring of the mixture of particulates and the mold inhibitory composition is maintained to effect an even application. Obviously, the temperatures and procedure noted above can be adjusted as desired to account for such factors as the batch size, the mold inhibitory composition used, the nature of any added hydrophobic material, the protein used, the size of the particulates, etc. Other appropriate conditions for preparing the composition can be obtained by using routine experimentation.

Microbial growth on a substrate material, i.e., the supplement, requires a certain degree of hydration, and in fact most molds except certain Aspergilli, require substantial moisture content in order to flourish. Application of a hydrophobic coating material to the supplement reduces hydration of the supplement, thus an essential precondition for rapid attack by molds in the compost is reduced. Substances which in appropriate circumstances may be used as a hydrophobic coating material in combination with the mold inhibitory composition include natural resins, such as shellac, natural waxes, such as beeswax and paraffin waxes; oils, such as vegetable and mineral oils; animal fats and synthetic low-melting or solvent-soluble polymers. The vegetable oils such as safflower, cottonseed, soybean, corn, olive, linseed, peanut, rape seed, sesame, wheat germ, sunflower seed, and palm oil can be used in the present invention. A preferred vegetable oil for use in the invention is corn oil used at a level between about 1% and 5%. As indicated above, both assimilable and nonassimilable hydrophobic materials may be used in the present invention. When using an assimilable material, however, high coating levels (generally above about 4-5%) should be avoided as such coating levels may tend to degrade performance. When coating the supplement with a hydrophobic material that contains mold inhibitory agents, cold oils may be used. This is greatly preferred from an economic standpoint, since no heating and cooling steps are required, reducing the processing time per batch, and allowing a continuous process.

When coating a particulate supplement with a natural wax, for example, a paraffin wax, sized pieces of the raw supplement are first placed in a vessel equipped for heating and stirring. The supplement can be pasteurized by heating the vessel to about 60° to 65° C. (140°-150° F.), while stirring the contents of the vessel. After an appropriate period at the pasteurization temperature, an appropriate amount of the paraffin wax, in molten form, is added to the vessel. A paraffin wax that can be processed at temperatures sufficiently low so as not to thermally degrade (i.e., denature) the nutrient is used. The contents of the vessel are cooled, accompanied by constant stirring, until the temperature falls below the congealing point of the wax. If necessary, an anti-caking agent, e.g., Celite, may be added to prevent the coated particulates from agglomerating.

While coating levels of hydrophobic material within the broad range of 2%-15% may be suitable in certain circumstances, we have found that coating levels between 4% and 11% yield the best results. As used in the specification and claims, the term "coating level" means the coating weight percent of a particular component based on the weight of the supplement substrate. For example, a paraffin wax coating level of 7% means that a quantity of paraffin wax coating material equal to 7% of the weight of the supplement substrate is applied as a coating.

The present invention also contemplates the addition of a supplement, or a combination of supplements, with different fractions having various amounts of the mold inhibitory composition and possibly various coating levels of additional hydrophobic material. Testing has shown that coating levels of the hydrophobic material between about 3% and 9%, are suitable for supplements applied at casing time, while coating levels between 7% and 11%, are appropriate for supplements applied at spawning, if no mold inhibitory composition is used. Lower levels may be suitable when using the mold inhibitory composition of the present invention.

In practicing various embodiments of this invention, a compost suitable for promoting the growth of mushroom mycelia is initially prepared. Details of this procedure need not be elaborated as they are well understood by one skilled in this art. The supplement of this invention is compatible with a wide variety of mushroom composts and is not to be limited to any particular composition. Suitable materials for preparing the compost include: horse manure, straw, corn cob, and other vegetative waste materials. The trays to be used for growing the mushrooms are then filled with the compost and the compost is thereafter impregnated with the mushroom mycelium. A wide variety of mushrooms can benefit from the supplement of this invention, and the invention is not limited to any particular mushroom species or strain thereof.

As noted above, the supplement can be applied either at the time of spawning or up to the time of casing the compost bed. When applying the supplement at spawning, the particulate supplement will generally be admixed into the compost bed with the mycelia. Application at spawning is preferred, since this procedure eliminates the additional labor associated with applying the supplement at casing. The supplement is provided in a particulate form that allows it to be added to the compost bed using available spawning equipment. For example, soybeans cracked to about 1/6 to 1/10 the size of the whole beans have been found to be suitable. Similarly, particulates made by pelletizing soybean fines also are suitable.

The supplement is generally added to the bed at a rate of from about 2% to about 8% based on the dry weight of the compost in the bed. The rate of application in any particular case is based on a number of factors including: the supplement used, the mushroom variety and the compost formulation. At low supplementation levels little improvement in yield is obtained, while as higher supplement application rates are used, the added mushroom yield per weight of added supplement decreases. Consequently, in any situation there will be economically defined lower and upper limits for the supplementation rate.

The spawned compost beds are then allowed to develop under carefully controlled conditions until the mycelia have completely permeated the compost. The present invention does not require any special provisions, and conditions normally employed for growing mushrooms can be advantageously employed. This process will usually take about two to four weeks. The beds are then cased with a layer of soil or peat. If the supplement was not added at the time of spawning, it is done at this time. This is done by admixing the supplement into the compost bed prior to applying the layer of casing material. Generaly, the first crop of mushrooms can then be harvested about three weeks after casing. The mushroom bed then goes through additional growth cycles in which additional mushrooms are produced. Generally, a commercial bed will undergo three to five such growth cycles before the compost is replaced.

As disclosed, the presence of the mold inhibitory composition prevents undesirable competition for the protein-containing nutrient. Unexpectedly, the composition does not adversely affect the yield of mushrooms. Indeed, under commonly encountered conditions in commercial mushroom farms, use of the present invention, and particularly the preferred combination of benzoic and undecylenic acids, improves the mushroom yield and compost quality even as compared to the use of particulate supplements treated just with a hydrophobic material.

When used, certain hydrophobic coatings may inhibit the growth of competing microorganisms on the supplement and may delay the availability of the nutrient to the mushroom mycelium, while the hydrophobic material is gradually removed under the conditions of mushroom growth. While we do not wish to be bound by theory, we believe that various microorganisms within the compost bed are capable of gradually breaking down the hydrophobic coating so as to gradually expose the nutrient supplement in a form suitable for assimilation by the mushroom mycelium. These microorganisms apparently comprise a portion of the organism population that survives the compost pasteurization step. While the compost is generally pasteurized to kill harmful pathogens, e.g., heating the compost for two to six hours at between about 60° to 65° C. (140°-150° F.) is typical, this treatment does not eradicate all of the organisms in the compost. For example, thermophilic and spore-forming microorganisms normally survive this treatment. Of the organisms surviving this treatment, there are apparently some capable of gradually degrading suitable hydrophobic coating materials, such as paraffin wax.

Throughout the specification and claims the phrase "gradually removed under the conditions of mushroom growth" is used to describe this process, as well as any other contributing processes by which the hydrophobic coating is gradually removed from the supplement.

As noted above, in another aspect of this invention, the mold inhibitory composition includes an additional hydrophobic material. The hydrophobic material can be conveniently admixed with the mold inhibitory composition before it is applied onto the nutrient. For example, in the case where a molten paraffin wax is used to coat cracked soybeans, the mold inhibitory composition can first be admixed into the molten wax. This mixture is then used to coat the soybeans according to the procedure described earlier. It also is possible to add the mold inhibitory composition to the supplement in cold oil coats. The most preferred coats include peanut or corn oils. Other procedures for coating the supplement with any particular mold inhibitory composition will be apparent to one skilled in the art.

The following examples will illustrate various working embodiments of the present invention.

EXAMPLE I

In this example, the results of small scale pot testing are described in which cracked soybeans were used as a nutrient supplement. The hulls, fines and extraneous weed seeds were removed from the cracked beans, which were then sieved to yield pieces averaging about 30 mg in size (about ⅛ of a whole bean). Various bean fractions were then coated with a variety of materials including beef tallow, clear shellac, orange shellac, beeswax and paraffin wax. All of the coatings were applied at a coating level of 5%, with the exception of one fraction which was coated with paraffin at 7%. In all, 10 samples were tested to determine their effect on mushroom growth.

The mushroom beds were prepared by adding 200 grams of compost, on a dry weight basis, having a 65% moisture content, to each pot. The pots were then spawned with mushroom mycelia of the species *Agaricus bisporus*. After allowing the mycelia suitable time to mature, the supplement was added to the pots and the compost beds were cased. Most of the supplements were added at a rate of 2%, although two samples, an orange shellac coated fraction and a clear shellac coated fraction, were applied at a rate of 6% and 8%, respectively. Six pots were prepared for each sample, with the exception of the clear shellac sample applied at a rate of 8% where only four pots were prepared because of a limited quantity of supplement material. Three breaks were obtained from each sample and the data are reported as the average total yield of the various replicates for each sample. An unsupplemented sample was used as a standard.

The results are presented in Table 1. As shown, the best results were obtained with the 7% paraffin coated sample, the orange shellac sample at a 6% supplementation rate and the clear shellac sample at an 8% supplementation rate, producing 29%, 50% and 64% increase in yields, respectively. The samples prepared with beef tallow and paraffin wax at a 5% coating level, and the basic clear and orange shellac coatings exhibited essentially no improvement relative to the unsupplemented sample in these tests. The clear and orange shellac samples in which the soybeans were soaked in 80% alcohol and the beeswax coated sample produced only marginal improvements of 9% and 17%, respectively.

TABLE 1

| SUPPLEMENT POT TESTING | |
|---|---|
| Coating | Yield (gram/pot) |
| Unsupplemented | 139 |
| Beef Tallow | 134 |
| Paraffin Wax | 137 |
| Clear Shellac | 141 |
| Orange Shellac | 148 |
| Clear Shellac[1] | 151 |
| Orange Shellac[1] | 151 |
| Beeswax | 162 |
| Paraffin Wax[2] | 180 |
| Orange Shellac[3] | 209 |
| Clear Shellac[4] | 228 |

[1]Soybeans preliminarily soaked in 80% alcohol
[2]7% coating level
[3]6% supplementation rate
[4]8% supplementation rate

EXAMPLE II

A number of tests were conducted in which a wide variety of soybeans were examined for their effect on mushroom growth. All of the soybeans were prepared in the manner described in Example I, and were coated with paraffin wax at a coating level of 7% using the procedure described earlier.

The same mushroom strain employed in Example I was used in these tests. The tests were also conducted in pots, each provided with 200 grams of compost on a dry basis. As in the previous examples, the mushroom beds were supplemented at casing at a rate of 4%. An unsupplemented sample was also prepared to serve as a standard.

The results are listed in Table 2. The data are presented as the 25 day percent conversion which is the weight of mushrooms produced per unit weight of dry compost in 25 days. This corresponded to three mushroom breaks. Improvements between 25% and 54% over the unsupplemented sample were obtained. This example illustrates a wide range of soybean varieties as mushroom supplements.

TABLE 2

| RELATIVE MUSHROOM YIELDS USING VARIOUS SOYBEAN VARIETIES | |
|---|---|
| Variety | 25 Day Conversion (%) |
| AgriPro 250 | 125 |
| Shawnee-11 | 120 |

TABLE 2-continued
RELATIVE MUSHROOM YIELDS USING VARIOUS SOYBEAN VARIETIES

| Variety | 25 Day Conversion (%) |
| --- | --- |
| SRF150 | 119 |
| RS 2300 | 119 |
| Gnome | 119 |
| Wayne | 117 |
| Beeson | 117 |
| Shawnee | 115 |
| SRF 307-P | 113 |
| Pilla | 111 |
| Wells 11-254 | 110 |
| AgriPro 26 | 108 |
| Williams 79 | 108 |
| AgriPro 27 | 108 |
| Williams | 107 |
| Amsoy 71-211 | 107 |
| Peterson 4880 | 107 |
| Asgrow 3127 | 106 |
| Vickery | 106 |
| AgriPro 25 | 104 |
| Washington V | 103 |
| Corsoy | 101 |
| Unsupplemented | 81 |

EXAMPLE III

This example describes results obtained using paraffin wax-coated soybean supplements. Five different grades of paraffin waxes were tested. The soybeans were initially prepared in the manner described in Example I and were then coated at four different coating levels, i.e., 4%, 5%, 6% and 7%, using the various waxes. The procedures described earlier for coating soybeans with a paraffin wax were used.

The same mushroom strain employed in earlier test work was used again. The tests were conducted in pots provided with 200 grams of compost on a dry basis. The mushroom beds were supplemented at casing at a rate of 4%. An unsupplemented sample was also prepared for comparison.

The results are presented in Table 3 as the weight of mushrooms produced in a supplemented tray per unit weight of mushrooms produced in the unsupplemented tray. The data indicate that yield incrases from 36% to 54% were obtained. These results show that a variety of paraffin waxes can be successfully used to coat the supplement.

TABLE 3
RELATIVE MUSHROOM YIELDS

| Paraffin Wax* | Coating Level (%) | | | | |
| --- | --- | --- | --- | --- | --- |
| | 4 | 5 | 6 | 7 | 8 |
| SR 125 q | 1.42 | 1.41 | 1.39 | 1.38 | 1.41 |
| FR 131 q | 1.45 | 1.50 | 1.53 | 1.52 | 1.48 |
| FR 335 M | 1.52 | 1.45 | 1.45 | 1.45 | 1.47 |
| MICRO 155 | 1.42 | 1.42 | 1.36 | 1.38 | 1.39 |
| MICRO 175 | 1.41 | 1.39 | 1.35 | 1.54 | 1.41 |

*Obtained from: Walnut-Hill, Inc., Green Lane and Wilson Avenue, P.O. Box 599, Bristol, PA 19007

EXAMPLE IV

In this example, the use of a component for inhibiting the growth of molds in a hydrophobic coating is described. Soybean supplements, preliminarily treated according to the procedure of Example I, were coated with paraffin wax at a coating level of 7%. Various amounts of benzoic acid were included in the molten wax and applied with the coating as a mold inhibitor. Mushroom mycelia of the species Agaricus bisporus were spawned into compost beds, which were then subsequently supplemented at casing with the above-prepared supplements at a 4% supplementation rate. Relative to an unsupplemented standard, these supplements improved the conversion after three breaks between 22% and 55%. More importantly, microbiological analysis showed that at a coating level of benzoic acid of 2% and above, mold growth was completely inhibited.

EXAMPLE V

In this example, the use of various combinations of undecylenic acid and benzoic acid used as a supplement coating is shown. Such supplements were applied to the mushroom bed at spawning time. Relative to a paraffin coated supplement (7% coating level) containing no mold inhibitory components which was applied to the mushroom bed at casing time, there was no diminution in yields. Results are shown in Table 4.

TABLE 4

| % undecylenic acid | % benzoic acid | | |
| --- | --- | --- | --- |
| | 0 | 1 | 2 |
| 6 | 112 | 110 | 118 |
| 8 | 109 | 107 | 111 |

The reported values represent percent conversions which are defined as weight of mushrooms produced per unit weight of dry compost times 100%. The rate of supplementation in the tests was 6%.

EXAMPLE VI

This example demonstrates the mold-inhibiting effect of the supplement coating additive consisting of 2% undecylenic acid and 1% benzoic acid.

Supplement pieces (cracked soybeans) with various coating compositions were incubated at 22° C. at 100% relative humidity for 10 days. At that time the number of pieces where mold growth was visible was determined (see Table 5).

TABLE 5

| % Coating | Composition of Coating | % of pieces with mold |
| --- | --- | --- |
| 0 | none | 100 |
| 7 | paraffin wax | 90 |
| 3 | 2 parts undecylenic acid, 1 part benzoic acid | 0 |
| 3 | 2 parts undecylenic acid, 1 part benzoic acid, 2 parts corn oil | 0 |

EXAMPLE VII

This example demonstrates the general susceptibility of microbial attack of the supplements with various coatings. Soybean pieces were placed on petri plates containing YAD medium (0.2% yeast extract, 2% agar, 2% glucose) and incubated at 20°14 22° C. After 11 days the number of pieces with mold or bacteria growing upon them was determined. the results are reported in Table 6.

TABLE 6

| % Coating | Composition of Coating | % of pieces with bacteria and mold |
| --- | --- | --- |
| 0 | | 100 |
| 7 | paraffin wax | 90 |

TABLE 6-continued

| % Coating | Composition of Coating | % of pieces with bacteria and mold |
|---|---|---|
| 3 | 2 parts undecylenic acid, 1 part benzoic acid, 2 parts corn oil | 15 |
| 3 | 2 parts undecylenic acid, 1 part benzoic acid | 0 |

While certain specific embodiments of the invention have been described with particularity herein, it will be recognized that various modifications thereof will occur to those skilled in the art. Therefore, the scope of the invention is to be limited solely by the scope of the appended claims.

What is claimed is:

1. A method for enhancing the growth of mushroom mycelia in a compost bed comprising admixing into said compost, either at the time of spawning of the mycelia or up to the time of casing, an effective amount of a particulate nutrient supplement comprising the combination of a protein-containing nutrient and a mold inhibitory composition.

2. The method of claim 1 wherein said mold inhibitory composition is selected from the group consisting of benzoic acid, undecylenic acid, and mixtures thereof.

3. The method of claim 2 wherein said mold inhibitory composition comprises benzoic acid and undecylenic acid each at a level of between about 1% and 8%.

4. The method of claim 1 wherein the particulate nutrient supplement is added to said compost bed at a supplementation rate of from about 2% to 8%.

5. The method of claim 4 wherein said protein-containing nutrient is cracked soybean.

6. The method of claim 4 wherein said protein-containing nutrient is pelletized soybean fines.

7. The method of claim 1 wherein said particulate supplement has a coating of a hydrophobic material.

8. The method of claim 7 wherein said hydrophobic material is not readily assimilable by competing microorganisms in the compost.

* * * * *